United States Patent [19]
Kalend et al.

[11] Patent Number: 5,823,192
[45] Date of Patent: Oct. 20, 1998

[54] APPARATUS FOR AUTOMATICALLY POSITIONING A PATIENT FOR TREATMENT/DIAGNOSES

[75] Inventors: Andre M. Kalend, Monroeville; Joel Greenberger, Sewickley; Karun B. Shimoga, Pittsburgh; Charalambos N. Athanassiou, Pittsburgh; Takeo Kanade, Pittsburgh, all of Pa.

[73] Assignee: University of Pittsburgh of the Commonwealth System of Higher Education, Pittsburgh, Pa.

[21] Appl. No.: 690,521

[22] Filed: Jul. 31, 1996

[51] Int. Cl.⁶ .................................................. A61G 15/00
[52] U.S. Cl. ........................................... 128/845; 128/846
[58] Field of Search ................................... 128/845, 846; 347/255, 260

[56] References Cited

U.S. PATENT DOCUMENTS

| | | | |
|---|---|---|---|
| 4,912,487 | 3/1990 | Porter | 347/255 |
| 4,935,635 | 6/1990 | O'Harra | 433/214 |
| 4,969,200 | 11/1990 | Manns | 382/288 |
| 4,979,223 | 12/1990 | Manns | 382/149 |
| 5,080,100 | 1/1992 | Trotel | 128/653.1 |
| 5,295,483 | 3/1994 | Nowacki et al. | 128/660.03 |
| 5,389,101 | 2/1995 | Heilbrun et al. | 606/130 |
| 5,446,548 | 8/1995 | Gerig et al. | 356/375 |
| 5,588,430 | 12/1996 | Bova et al. | 128/653.1 |

Primary Examiner—Michael A. Brown
Attorney, Agent, or Firm—Richard V. Westerhoff; Eckert Seamans Cherin & Mellott, LLC

[57] ABSTRACT

A patient is automatically accurately positioned relative to a fixed reference of a treatment/diagnostic device by an optical system which operates a patient positioning assembly to bring fiducials or skin markers on the patient into coincidence with impingement points of laser beams projected in a fixed pattern relative to the device. Cameras record images of the fiducials and laser impingement points from which alignment error and velocity error in pixel space are determined. The velocity error in pixel space is converted to a velocity error in room space by the inverse of an Image Jacobian. The Image Jacobian is initially derived using rough values for system parameters and is continuously updated and refined using the calculated errors in pixel space derived from the camera images and errors in room space derived from position encoders on the treatment/diagnostic device.

12 Claims, 15 Drawing Sheets

APPARATUS FOR AUTOMATICALLY POSITIONING A PATIENT FOR TREATMENT/DIAGNOSES

BACKGROUND OF THE INVENTION

1. Field of the Invention

This invention relates to an apparatus for automatically positioning a patient reclining on a movable couch assembly relative to treatment/diagnoses equipment, such as radiation therapy equipment

2. Background Information

In conformal radiation therapy, a beam of high energy radiation is directed at a tumor from different angles to maximize irradiation of the tumor while minimizing the exposure of surrounding healthy tissue. Both the couch on which the patient reclines and the linear accelerator which delivers the beam of radiation are moved to generate the multiple treatment beams.

Prior to treatment with the high energy beam, a simulation is performed on a similar machine using low level radiation in order to establish a repeatable relationship between the location of the tumor and a reference frame of the machine. In order to assure that the same relationship is repeated on the treatment machine, an optical system is used to establish the orientation of the patient relative to the machine frame of reference. This has been accomplished by the use of three laser beams projected in a common reference plane and intersecting at the machine isocenter. The machine isocenter is the point through which the radiation beam passes for all positions of the linear accelerator. Typically, two of the beams are directed horizontally in opposite directions and the third beam is directed vertically downward from the ceiling.

For establishing patient position, the couch assembly is positioned so that this treatment plane passes thorough the treatment site. For example, for a tumor in the chest, the couch is positioned so that with the patient supine, the treatment plane passes transversely through the chest and the three laser beams will impinge upon the anterior and each side of the patient's chest. Skin markers or fiducials are applied to the patient at the points where the three laser beams impinge. When the patient is then transferred to the treatment machine and is placed in roughly the same position relative to the treatment plane, errors in placement will be indicated by the distance between the skin markers or fiducials and the laser markers or points where the laser beams impinge upon the patient. Currently, a technician manually jogs the couch assembly, and perhaps adjusts patient position on the couch, until the fiducials are coincident with the points of impingement of the laser beams. This requires coordination of movements in the 4 degrees of freedom of the couch assembly which requires dexterity and is time consuming. It also limits the ability to treat multiple tumors or diffuse pathologies which required multiple patient alignments.

In complex conformal radiation therapy, the treatment site is positioned at a virtual isocenter displaced along the radiation beam from the true isocenter. This further complicates moving the couch assembly in its four degrees of freedom in order to bring the three fiducials into coincidence with the impingement points of the laser beams. This alignment of the patient must be repeated precisely when multiple treatments are performed.

There are known robot positioning systems being developed in laboratories which are controlled by video cameras. Typically, these systems require a precise knowledge of a large number of system parameters. Such systems are not only difficult to set up, but any change in the components, even the exchange of a camera for an identical model, requires recalibration. Furthermore, disturbance of the system such as an inadvertent bumping of a component can require recalibration.

There is a need therefore for apparatus for automatically positioning a patient relative to treatment/diagnoses devices.

There is need for such apparatus which can rapidly and accurately position the patient, and do so without uncomfortable or erratic movements. There is an additional need for such apparatus which does not require precise measurement of positioning system parameters and which does not require recalibration when any of the components are changed or accidently disturbed.

SUMMARY OF THE INVENTION

These needs and others are satisfied by the invention which is directed to apparatus for automatically, accurately positioning a patient reclining on a moveable patient positioning assembly to a fixed base position relative to a fixed reference point of a treatment/diagnostic device. The apparatus includes a plurality of spaced apart fiducials arranged on the patient. These fiducials or skin markers can be artificially applied marks or naturally occurring identifiable markings on the patient's skin. Laser beam generator means generates a plurality of laser beams projected in different directions relative to the fixed reference point to impinge on the patient at impingement points which coincide with the fiducials when the patient is at the fixed base position. Camera means generate images of the fiducials and the impingement points. Means for generating control signals from the camera images drive the moveable patient positioning assembly to bring the fiducials into coincidence with the impingement points, thereby positioning the patient at the fixed base position. Preferably, the laser beam generator means comprises means generating three laser beams orthogonally projected in the treatment plane of the machine to intersect at the machine's isocenter. These may be a pair of opposed horizontal beams and a beam projected vertically downward. In this case, three fiducials are arranged on the patient to be coincident with the impingement points of the laser beams on the patient when in the base position.

Where the patient positioning assembly is unable to rotate the supine patient about a longitudinal axis or tilt the patient about a lateral axis so that the patient positioning assembly only has four degrees of freedom, two laser beam generators generating two non-parallel beams, two fiducials and two cameras are adequate to uniquely position the patient.

Preferably, the means generating the control signals from the images produced by the cameras comprises means generating signals representing positions of the fiducials and impingement points in two-dimensional pixel space, and means generating the control signals in three-dimensional room space from signals in pixel space, including means applying conversion means converting signals in pixel space to signals in room space. In addition, means are provided for continuously updating or refining the conversion means. This includes means establishing a last approximate conversion means, means setting the patient positioning assembly in motion, means repetitively determining present position error of the fiducials relative to the laser impingement points in pixel space at specified sample times, means repetitively determining a present position error between the fiducials and the laser impingement points in room space at the sample times, and means updating the conversion means from the present position error in pixel space and the present position error in room space. The means generating control signals from the images includes means repetitively generating a velocity error signal in pixel space from the position signals in pixel space and the conversion means comprises velocity conversion means converting the velocity error signal in pixel space to a velocity error signal in room space for controlling driving the patient positioning assembly to bring the fiducials into coincidence with the impingement points.

The means continuously refining the conversion means comprises means establishing a rough initial value of the conversion means, means repetitively determining a present position error in the fiducials relative to the laser impingement points in pixel space from the images of the fiducials and the impingement points, means repetitively determining a present position error between the fiducials and the laser impingement points in room space from the output of position encoders on the patient positioning assembly, and means updating the conversion means from the present position error in pixel space and the present position error in room space.

The conversion means comprises means applying an inverse of an Image Jacobian to the velocity error signal in pixel space to generate a velocity error signal in room space for driving the patient positioning assembly. The means continuously refining the conversion means comprises means repetitively at the sampling intervals updating the Image Jacobian according to a specified relationship. This arrangement requires no detailed calibration of the cameras as in the prior art which required perfect knowledge of the position of the cameras and accurate knowledge of their parameters such as for instance, focal length.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENT

Figure 1:
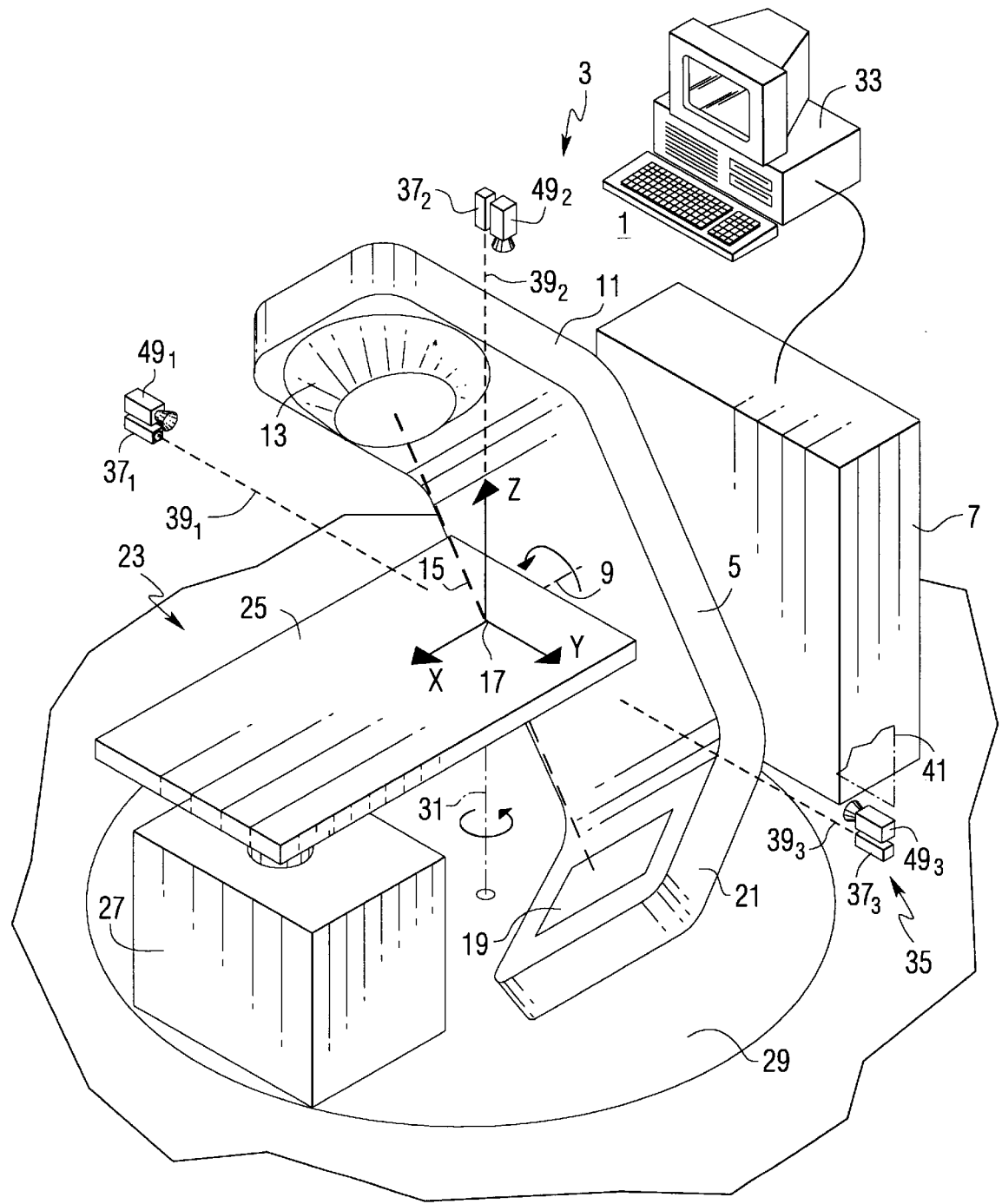
FIG. 1 is an isometric view of an arrangement for performing dynamic conformal radiation therapy utilizing the invention.

FIG. 1 illustrates apparatus 1 for implementing the invention. This apparatus 1 includes a machine 3 having a gantry 5 pivotally mounted on a machine base 7 for rotation about a horizontal axis 9. The gantry 5 has a first arm 11 carrying a collimator 13 which directs a beam of high energy radiation 15 such as a beam of high energy photons along a path which is perpendicular to and passes through an extension of the axis of rotation 9. This intersection is referred to as the isocenter 17. In some machines, a portal imager 19 is mounted on a second arm 21 on the opposite end of the gantry in alignment with the radiation beam 15. The portal imager 21 records radiation which is not absorbed by the patient.

The isocenter 17 serves as the origin of a coordinate system for room space. As can be seen, the X axis coincides with the axis of rotation 9 of the gantry. Thus, as the gantry rotates it defines a plane of treatment containing the Y and Z axes.

The machine 3 further includes a patient positioning assembly 23 which includes a couch 25 mounted on a support 27 for vertical, lateral and longitudinal movement relative to the support. The support is mounted on a turn table 29 which has its axis 31 vertically aligned under the isocenter 17 and concentric with the Z axis. With this arrangement, the patient positioning assembly 23 has four degrees of freedom: in the X, Y and Z axes of room space and rotation about the z axis. Thus, the patient is not rotated about the longitudinal axis of the couch or tilted about a horizontal axis extending transversely through the couch. However, with the addition of rotation of the gantry in the Y–Z treatment plane, the radiation beam 15 can be directed through a patient reclining on the couch 25 in any desired direction. A computer 33 controls movement of the patient positioning assembly 23, in a manner to be described, to align the patient at a fixed base position relative to a machine reference point which is typically the isocenter 17.

In practicing conformal radiation therapy, the patient is placed on the couch 25 of a similar machine which generates a low energy beam such as an x-ray beam for establishing the progression of high energy treatment beams to be used. In order to precisely align the patient on a treatment machine in the same orientation as on the low level simulation machine, an optical alignment system 35 is used. This system includes a plurality of laser beam generators, in the illustrative case three laser beam generators $37_1$, $37_2$, and $37_3$ mounted at fixed positions within the treatment room. In the example, the laser beam generators $37_1$, $37_2$ and $37_3$ project laser beams $39_1$, $39_2$, and $39_3$ in a common reference plane 41 which is coincident with the Y–Z treatment plane of the machine 3 and which all intersect at the isocenter 17.

Figure 2:
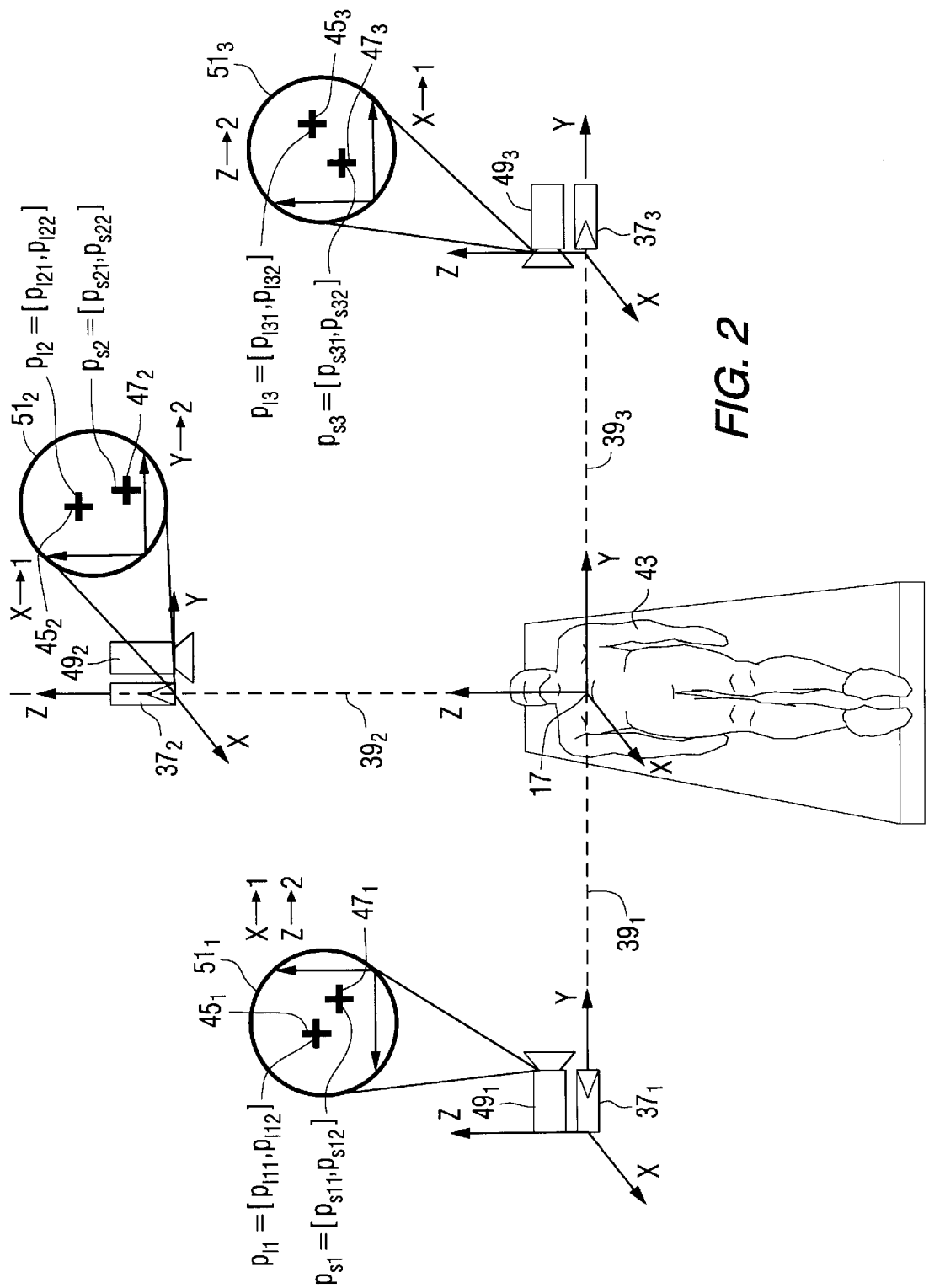
FIG. 2 is a schematic diagram illustrating the generation of camera images in accordance with the invention.
Figure 2A:
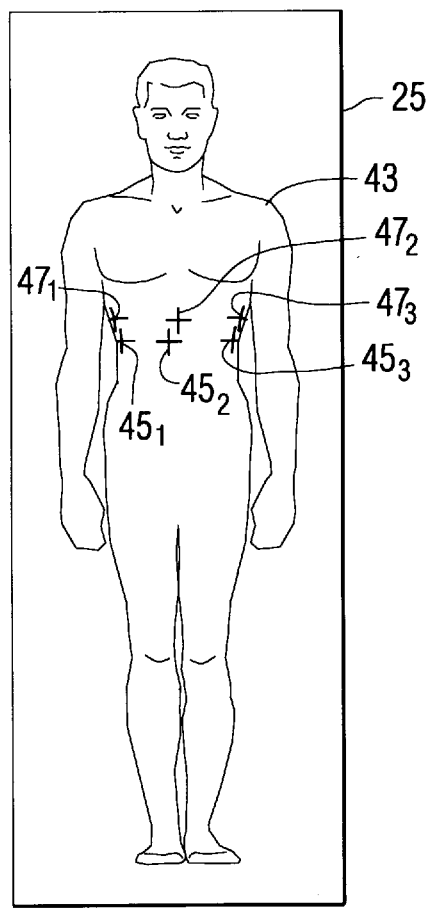
FIG. 2a is a plan view illustrating the location of markers used to position a patient in accordance with the invention.

As shown in FIG. 2, the laser beams $39_1$, $39_2$, and $39_3$ impinge upon a patient 43 supine upon the couch 25 at three impingement points $45_1$, $45_2$, and $45_3$ as shown in FIG. 2a. These impingement points or laser markers are in the form of cross-hairs in the illustrative embodiment of the invention. Skin markers such as fiducials $47_1$, $47_2$, and $47_3$ are placed on the patient at the impingement points, which in the example, are on the anterior and each side of the chest. These three fiducials or skin markers remain on the patient throughout the treatment course, and are used to precisely align the patient on the treatment machine in the same orientation as on the simulation machine, and for successive treatments. In order to bring the patient into proper alignment, the patient positioning assembly 23 is moved in its four degrees of freedom as necessary to drive the fiducials $47_1$, $47_2$, and $47_3$, and the corresponding impingement points $45_1$, $45_2$, and $45_3$ into coincidence.

In accordance with the invention, this alignment of the patient is performed automatically. To this end, the optical alignment system 35 further includes three video cameras, $49_1$, $49_2$, and $49_3$ mounted adjacent associated laser beam generators $37_1$, $37_2$, and $37_3$ and aligned to generate images $51_1$, $51_2$, and $51_3$ of the respective impingement points $45_1$, $45_2$, and $45_3$ and the corresponding fiducials $47_1$, $47_2$ and $47_3$. These images are generated in pixel space as shown in FIG. 2. Pixel space is the two-dimensional space of the plane of the camera image, so called because of the pixels which generate the image. The images of the impingement points and fiducials are used in a proportional control scheme to generate the desired motion of the patient positioning assembly 23 so as to gradually reduce the position error of all three fiducials to zero. This control scheme includes the generation and use of an Image Jacobian which is a matrix relating velocities of feature points in room space to velocities of the corresponding feature points in pixel space. The control signal generated for room space is then converted to joint motor input signals using existing patient positioning assembly control hardware. The corrective action, starting with the camera images and ending in patient positioning assembly motion, is repeated at a frame rate which in the example is 30 Hz until all three fiducials have negligible error. In other words, until the patient is well aligned. Alignments with this system can be made accurately to within about a millimeter or better.

Each of the cameras $49_1$, $49_2$, and $49_3$ generates a two-dimensional image of one of the fiducials $47_1$, $47_2$, $47_3$ and the corresponding laser impingement point $45_1$, $45_2$, and $45_3$. Each of these images $51_1$, $51_2$, and $51_3$ is generated in a different two-dimensional plane. These locations are transformed into a camera pixel space frame of reference. For instance, the location of the first laser impingement point $45_1$ in pixel space is represented by an X coordinate $p_{l11}$, and a Z coordinate $p_{l12}$ as indicated in FIG. 2 where a convention has been selected in which the X coordinate is represented by a 1 in the last subscript and the Z coordinant by a 2. Similarly, the fiducial or skin marker seen by the first camera $47_1$ is located at the point $P_{sl}$ having the coordinates $p_{s11}$ and $p_{s12}$ in the X–Z plane of the camera $49_1$. The images $51_2$ generated by the second camera $49_2$ for the second laser impingement point $45_2$ and the second fiducial $47_2$ are represented by the points $p_{l2}$ and $p_{s2}$, respectively in the X and Y plane. Also, the images $51_3$ of the third impingement point $45_3$ and fiducial $47_3$ seen by the third camera $49_3$ are identified as the points $p_{l3}$ and $p_{s3}$ having X and Z coordinates.

Figure 3:
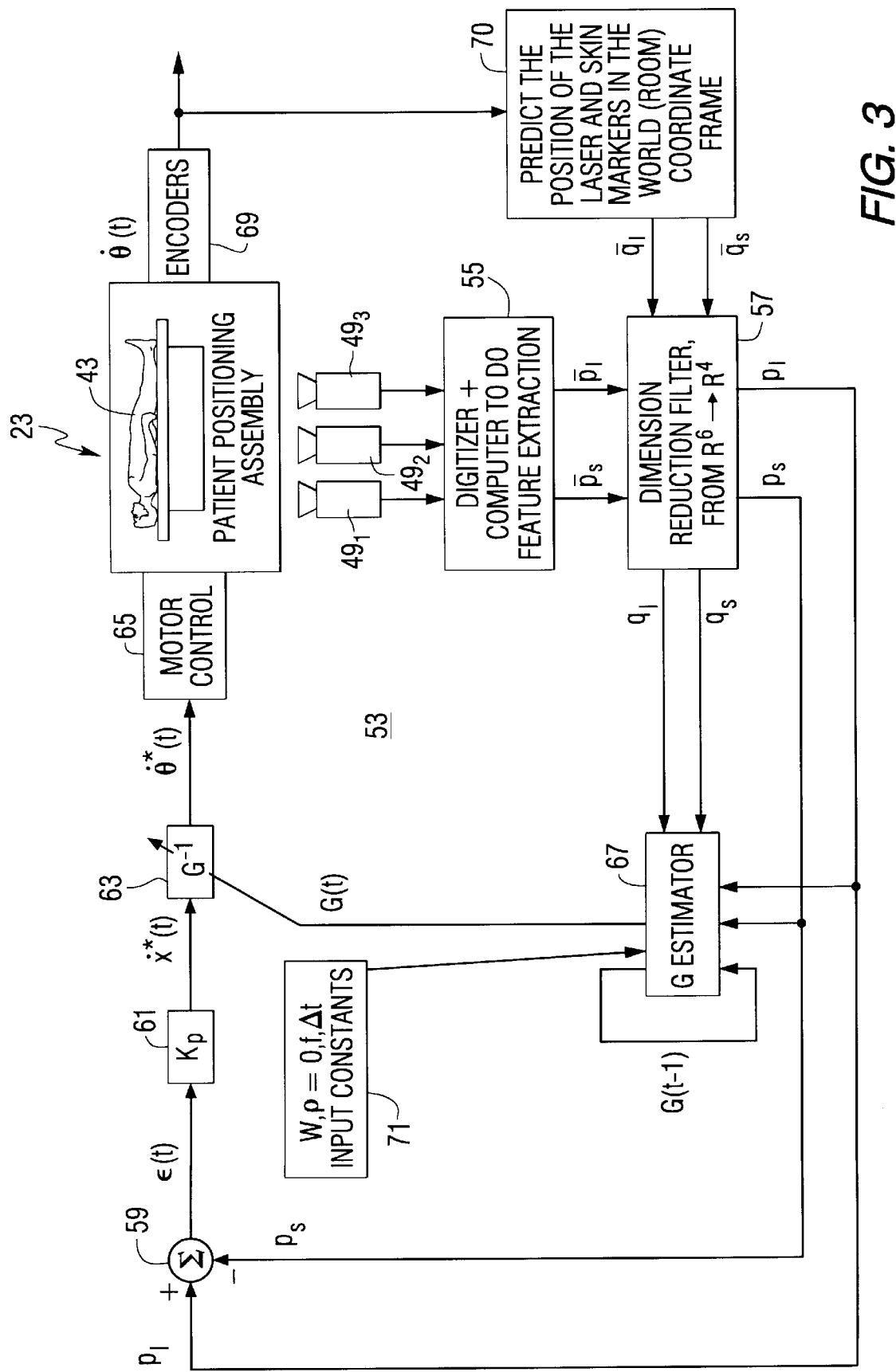
FIG. 3 is a schematic diagram of a feedback control loop in accordance with an illustrated embodiment of the invention.

A schematic diagram of the alignment control scheme 53 is illustrated in FIG. 3. The three camera $49_1$–$49_3$ generate images of the three sets of fiducials and laser impingement points. A feature extraction computer 55 digitizes the signals from the cameras and extracts the two-dimensional locations of the fiducials and laser impingement points in pixel space. This computer provides as an output the following six-dimensional vectors $\bar{p}_l$ and $\bar{p}_s$ representing the locations of the laser impingement points and skin markers or fiducials respectively in pixel space:

$$\bar{P}_l = \{P_{l11} P_{l12} P_{l21} P_{l12} P_{l31} P_{l32}\} \in R^6 \quad\quad 1$$

$$\bar{P}_s = \{P_{s11} P_{s12} P_{s21} P_{s22} P_{s31} P_{s32}\} \in R^6 \quad\quad 2$$

Since as mentioned the patient positioning assembly 23 only has 4 degrees of freedom, the six-dimensional vectors $\bar{p}_l$ and $\bar{p}_s$ can be reduced to four-dimensional vectors $p_l$ and $p_s$. In determining which of the terms of equations 1 and 2 can be eliminated, it will be observed from FIGS. 1 and 2 that since the three fiducials $47_1$–$47_3$ or skin markers on the patient define a plane, and since the patient positioning assembly 23 cannot rotate about the Y axis, alignment of the two side fiducials $47_1$–$47_3$ in the X direction necessarily aligns the third fiducial $47_2$ in the X direction. Therefore, the term $p_{s21}$ can be eliminated from equation 2 and the corresponding term $p_{l21}$ can be eliminated from equation 1. Also, since the patient positioning assembly 23 cannot rotate the patient about the X axis, the Z dimension of the side fiducials, $47_1$ and $47_3$ change by the same amount when the couch is raised or lowered and therefore movement of only one in the Z direction needs to be controlled. While either of the term $p_{s12}$ or $p_{s32}$ could be eliminated, the latter has been eliminated in the illustrative system along with the corresponding term $P_{l32}$.

Thus, the six-dimensional vectors of equations 1 and 2 are reduced to the following four-dimensional vectors by a dimension reduction filter 57.

$$P_l = \{P_{l11} P_{l12} P_{l22} P_{l31}\} \in R^4 \quad\quad 3$$

$$P_s = \{P_{s11} P_{s12} P_{s22} P_{s31}\} \in R^4 \quad\quad 4$$

These four-dimensional vectors $p_s$ and $p_l$ representing the positions of the fiducials and laser impingement points, respectively, in pixel space are subtracted at 59 to determine the position error $\epsilon(t)$ in pixel space. Proportional control represented by the gain $K_p$ is applied to this position error at 61 to generate a command velocity $\dot{x}^*(t)$ in pixel space as follows:

$$\dot{x}^*(t) = K_p \epsilon(t) \quad\quad 5$$

where $K_p$ is a 4×4 matrix of the proportional error gain.

The command velocity $\dot{x}^*(t)$ in pixel space is converted to a command velocity $\dot{\Theta}^*(t)$ in room space through a conversion mechanism 63 which is a 4×4 matrix known as the inverse of the Image Jacobian G. The command velocity $\dot{\Theta}^*(t)$ in room space is a four dimensional vector which is applied to the motor control 65 of the patient positioning assembly 23. In the illustrative patient positioning assembly, the motor control 65 is a velocity control which controls the joint motors of the positioning assembly to drive the fiducials toward coincidence with the laser impingement points.

As mentioned, the Image Jacobian G can be generated by explicit computation which requires accurate calibration of the camera and surrounding environment, a procedure involving accurate determination of dozens of parameters. In accordance with the invention, G is obtained by on-line estimation in a G estimator 67 using input-output errors. As will be discussed in more detail below, G is continuously updated by incrementally adjusting the last value of the matrix. This is accomplished using the fiducial position error in pixel space $\epsilon(t)$ from laser impingement point position in pixel space $p_l$ and fiducial position in pixel space $p_s$, and position error in room space $\delta(t)$ derived from the output of position encoders 69 on the patient positioning assembly 23. The encoder outputs are used to generate the predicted positions of $\bar{q}_l$ and $\bar{q}_s$ of the laser beam impingement points and the fiducials in room space. The vector $\bar{q}_l$ and $\bar{q}_s$ are generated by approximating the locations of the three fiducials relative to the table using average values for the size of the patients and the normal positioning of the patient on the couch. Knowing the table location (X, Y, Z, θ) in room space, the locations of the fiducials $47_1$, $47_2$ and $47_3$ in room space can be calculated as:

$$\bar{q}_{s1} = \{q_{s1x} q_{s1y} q_{s1z}\} \quad\quad 6$$

$$\bar{q}_{s2} = \{q_{s2x} q_{s2y} q_{s2z}\} \quad\quad 7$$

$$\bar{q}_{s3} = \{q_{s3x} q_{s3y} q_{s3z}\} \quad\quad 8$$

Some of the components of these vectors do not have to be considered explicitly. For example, as can be understood from reference to FIGS. 2 and 2a, the camera $49_1$ can only determine the X and Z components of the fiducial $47_1$ and does not observe the Y component. Thus, $q_{s1y}$ is not controllable. Similarly, the camera $49_2$ can not observe the Z position of the fiducial $47_2$ and the camera $49_3$ cannot see the Y position of the fiducial $47_3$ and therefore these terms are also uncontrollable. Eliminating these terms and combining equations 6 through 8, we get:

$$\bar{q}_s = \{q_{s1x}, q_{s1z}, q_{s2x}, q_{s2y}, q_{s3x}, q_{s3z}\} \qquad 9$$

In a similar manner, the positions of the laser markers or impingement points $45_{1-3}$ are:

$$\bar{q}_{l1} = \{q_{l1x}, q_{l1y}, q_{l1z}\} \qquad 10$$

$$\bar{q}_{l2} = \{q_{l2x}, q_{l2y}, q_{l2z}\} \qquad 11$$

$$\bar{q}_{l3} = \{q_{l3x}, q_{l3y}, q_{l3z}\} \qquad 12$$

For the reasons discussed above, the elements $\bar{q}_{l1y}$, $q_{l2z}$ and $q_{l3z}$ and $q_{s3z}$ and Equations 10–12 are unobservable. Dropping these elements and combining equations 10–12 yields:

$$\bar{q}_l = \{q_{l1x}, q_{l1z}, q_{l2x}, q_{l2y}, q_{l3x}, q_{l3z}\} \qquad 13$$

As discussed above, the patient positioning assembly 23 only has 4° of freedom and hence the six-dimensional vectors of Equation 9 and 13 can be reduced to four-dimensional vectors by the elimination of the terms $q_{s2x}$, $q_{s3z}$, $q_{l2x}$ and $q_{l3z}$ for the same reasons discussed in connection with the reduction of the vectors for fiducial and impingement point positions in pixel space discussed above. Thus, the four-dimensional vectors representing the positions of the fiducials and impingement points in room space become:

$$q_s = \{q_{s1x}, q_{s1z}, q_{s2y}, q_{s3x}\} \qquad 14$$

$$q_l = \{q_{l1x}, q_{l1z}, q_{l2y}, q_{l3x}\} \qquad 15$$

It should be noted that since the laser beams $39_1$ and $39_3$ are projected along the Y axis of room space and the beam $39_2$ is projected along the Z axis, that all of the elements of $q_1$ in Equation 15 will be zeros in the exemplary embodiment of the invention.

The G estimator 67 also utilizes several constants indicated at 71 as including a matrix W which is a weighing factor controlling the rate of convergence of the position of the fiducials to the position of the laser impingement points, a factor p known as a "forgetting factor" which determines the relative weight of past calculations of G, rough values of the focal lengths of the cameras f, and the sampling interval $\Delta t$. The sampling interval as indicated above is 30 Hz in the illustrative system.

While the Image Jacobian G can be derived solely from the relevant parameters, it is appropriate to provide an initial value to reduce the time required to obtain a refined value and to smooth the initial movements of the patient positioning assembly 23. However, only a rough estimation of the needed parameters is required. The quality of this initial approximation affects only the speed of convergence of the apparatus and only the first time, since afterwards the last best estimate made is reused and refined. These initial parameters include the following:

(i) Focal lengths of the three cameras (m):
  $f_1, f_2, f_3$.
(ii) Pixel sizes of the three cameras (m):
  $(S_{1x}, S_{1z}), (S_{2x}, S_{2y}), (S_{3x}, S_{3z})$
(iii) Positions of fiducials in camera space (m):
  $\{^cX_1 {}^cY_1 {}^cZ_1\}$, $\{^cX_2 {}^cY_2 {}^cZ_2\}$, $\{^cX_3 {}^cY_3 {}^cZ_3\}$
(iv) Positions of fiducials in room space (m):
  $\{^TX_1 {}^TY_1 {}^TZ_1\}$, $\{^TX_2 {}^TY_2 {}^TZ_2\}$, $\{^TX_3 {}^TY_3 {}^TZ_3\}$ Using these parameters, the positions of the skin markers or fiducials in pixel space are determined as follows:

$$\text{Camera } 49_1: X_{S1} = \left(\frac{f_1 \cdot {}^cX_1}{(S_{1x} \cdot {}^cY_1)}\right); Z_{S1} = \left(\frac{f_1 \cdot {}^cZ_1}{(S_{1z} \cdot {}^cY_1)}\right) \qquad \text{Eq. 16}$$

$$\text{Camera } 49_2: X_{S2} = \left(\frac{f_2 \cdot {}^cX_2}{(S_{2x} \cdot {}^cX_2)}\right); Y_{S2} = \left(\frac{f_2 \cdot {}^cY_1}{(S_{2Y} \cdot {}^cZ_2)}\right) \qquad \text{Eq. 17}$$

$$\text{Camera } 49_3: X_{S3} = \left(\frac{f_3 \cdot {}^cX_3}{(S_{3x} \cdot {}^cX_3)}\right), Z_{S3} = \left(\frac{f_3 \cdot {}^cZ_3}{(S_{3z} \cdot {}^cY_3)}\right) \qquad \text{Eq. 18}$$

The elements of the Image Jacobian Matrix G are then calculated as follows:

$$G_{11} = (f_1/(S_{1X} \cdot {}^cY_1)) \qquad \text{Eq. 19}$$

$$G_{12} = -(X_{S1}/{}^cY_1) \qquad \text{Eq. 20}$$

$$G_{13} = 0 \qquad \text{Eq. 21}$$

$$G_{14} = -\left(\frac{X_{S1} \cdot {}^TX_1}{{}^cY_1} + \frac{f_1 \cdot {}^TY_1}{S_{1X} \cdot {}^cY_1}\right) \qquad \text{Eq. 22}$$

$$G_{21} = 0 \qquad \text{Eq. 23}$$

$$G_{22} = -(Z_{S1}/{}^cY_1) \qquad \text{Eq. 24}$$

$$G_{23} = (f_1/(S_{1Z} \cdot {}^cY_1)) \qquad \text{Eq. 25}$$

$$G_{24} = -\left(\frac{Z_{S1} \cdot {}^TX_1}{{}^cY_1}\right) \qquad \text{Eq. 26}$$

$$G_{31} = 0 \qquad \text{Eq. 27}$$

$$G_{32} = (f_2/(S_{2Y} \cdot {}^cZ_2)) \qquad \text{Eq. 28}$$

$$G_{33} = -(Y_{S2}/{}^cZ_2) \qquad \text{Eq. 29}$$

$$G_{34} = \left(\frac{f_2 \cdot {}^TX_2}{S_{2Y} \cdot {}^cZ_2}\right) \qquad \text{Eq. 30}$$

$$G_{41} = (f_3/(S_{3X} \cdot {}^cY_3)) \qquad \text{Eq. 31}$$

$$G_{42} = -(X_{S3}/{}^cY_3) \qquad \text{Eq. 32}$$

$$G_{43} = 0 \qquad \text{Eq. 33}$$

$$G_{44} = -\left(\frac{X_{S3} \cdot {}^TX_3}{{}^cY_3} + \frac{f_3 \cdot {}^TY_3}{S_{3X} \cdot {}^cY_3}\right) \qquad \text{Eq. 34}$$

The Image Jacobian matrix G is then constructed as follows:

$$G = \begin{bmatrix} G_{11} & G_{12} & G_{13} & G_{14} \\ G_{21} & G_{22} & G_{23} & G_{24} \\ G_{31} & G_{32} & G_{33} & G_{34} \\ G_{41} & G_{42} & G_{43} & G_{44} \end{bmatrix} \qquad \text{Eq. 35}$$

Figure 4:
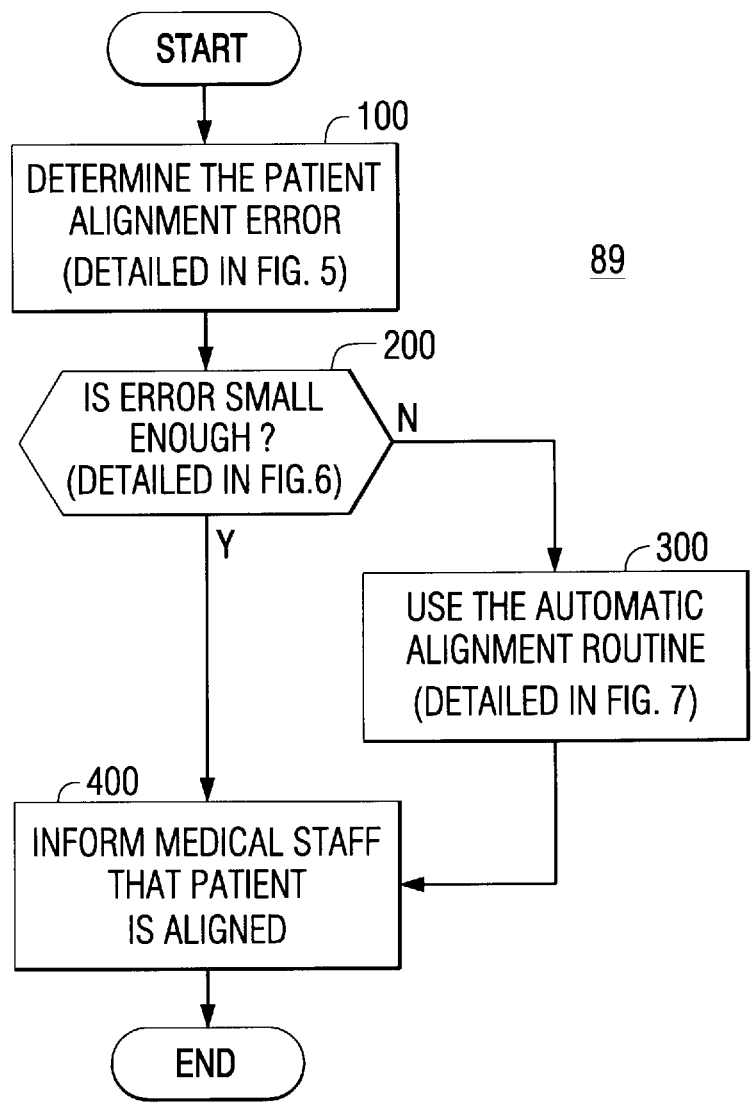
FIGS. 4–16 are flow charts of software routines which form part of the invention.
Figure 5:
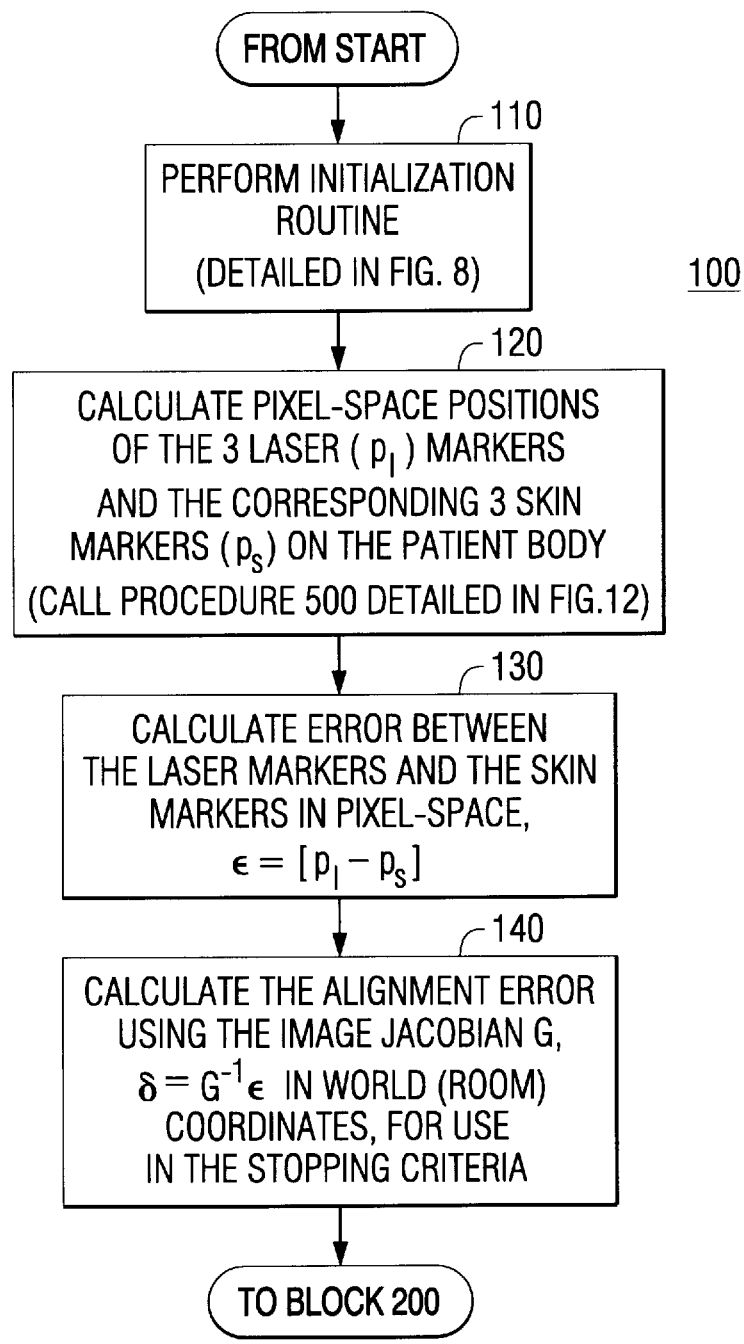

The alignment control scheme 53 is implemented by the computer 33 using the software which is illustrated in flow chart form in FIGS. 4–16. FIG. 4 illustrates the main routine 99. This main routine includes determining the patient alignment error as indicated at 100. If the error in the position of all of the fiducials $47_1$–$47_3$ relative to the corresponding laser beam impingement points $45_1$–$45_3$ is less than a threshold value as determined at 200, then an output is generated at 400 informing the medical staff that the patient is aligned. Otherwise, the automatic optical alignment routine is utilized at 300. The details of the routine 100 for determining the patient alignment error are shown in FIG. 5. An initialization routine which is detailed in FIG. 8 is performed at 110. The positions of the laser markers and corresponding skin markers or fiducials are then calculated at 120 using the procedure 500 detailed in FIG. 12. These marker positions are then used in block 130 to calculate the error between the laser markers and skin markers in pixel space. The alignment error in room space δ is then calculated in 140 using the error ε in pixel space and the inverse of the Image Jacobian $G^{-1}$.

Figure 6:
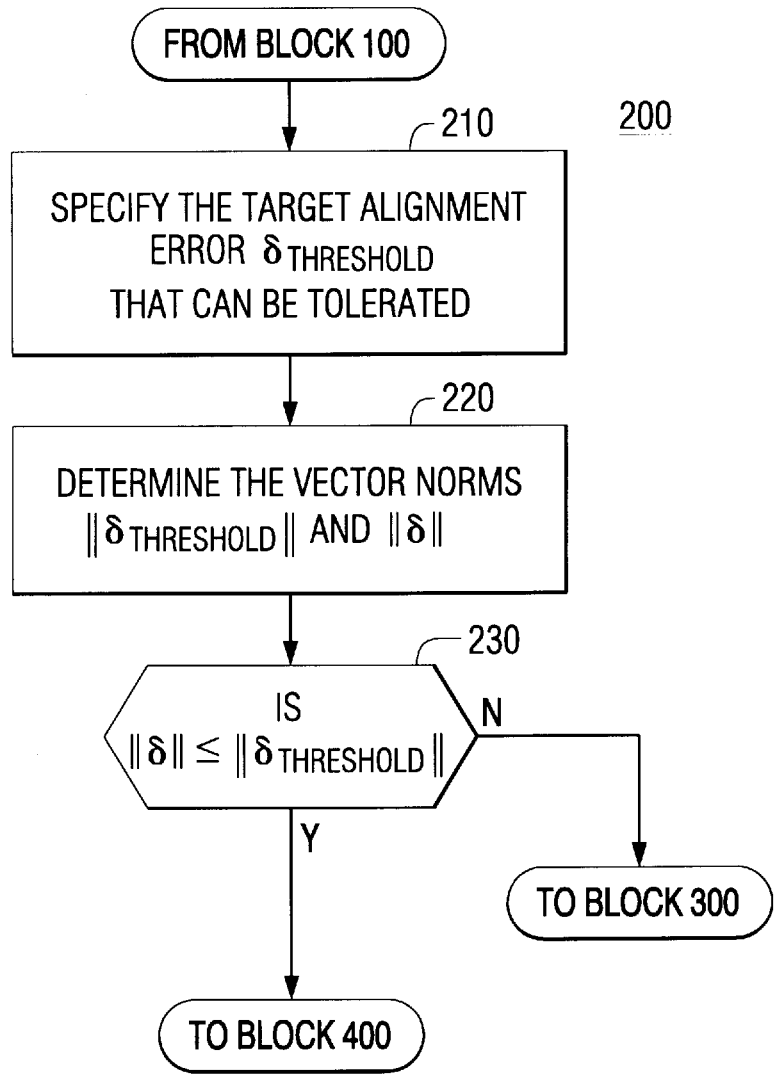

FIG. 6 illustrates the details of the block 200 in FIG. 4 which determines whether the alignment error in the room space has been reduced to the point at which the patient is considered to be aligned. The amount of alignment error $\delta_{threshold}$ that can be tolerated is specified at 210. The vector norms of $\delta_{threshold}$ and δ (calculated in block 140) are determined in block 220 and compared in block 230. A exemplary value for the norm of $\delta_{threshold}$ is about 1 millimeter. If the calculated position error is less than the threshold value then the alignment is completed at block 400 in FIG. 1. Otherwise, automatic alignment is initiated at 300 in FIG. 1.

Figure 7:
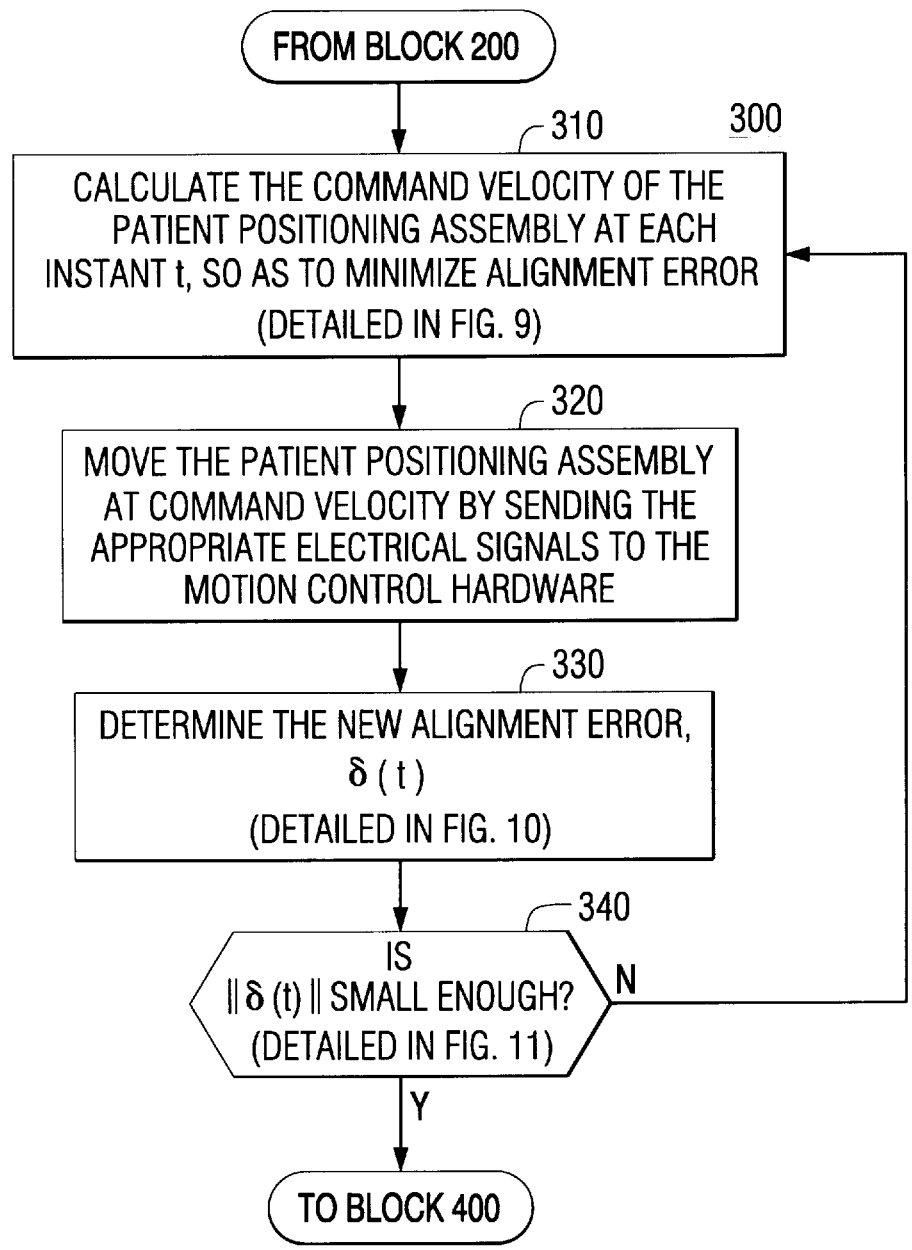
Figure 8:
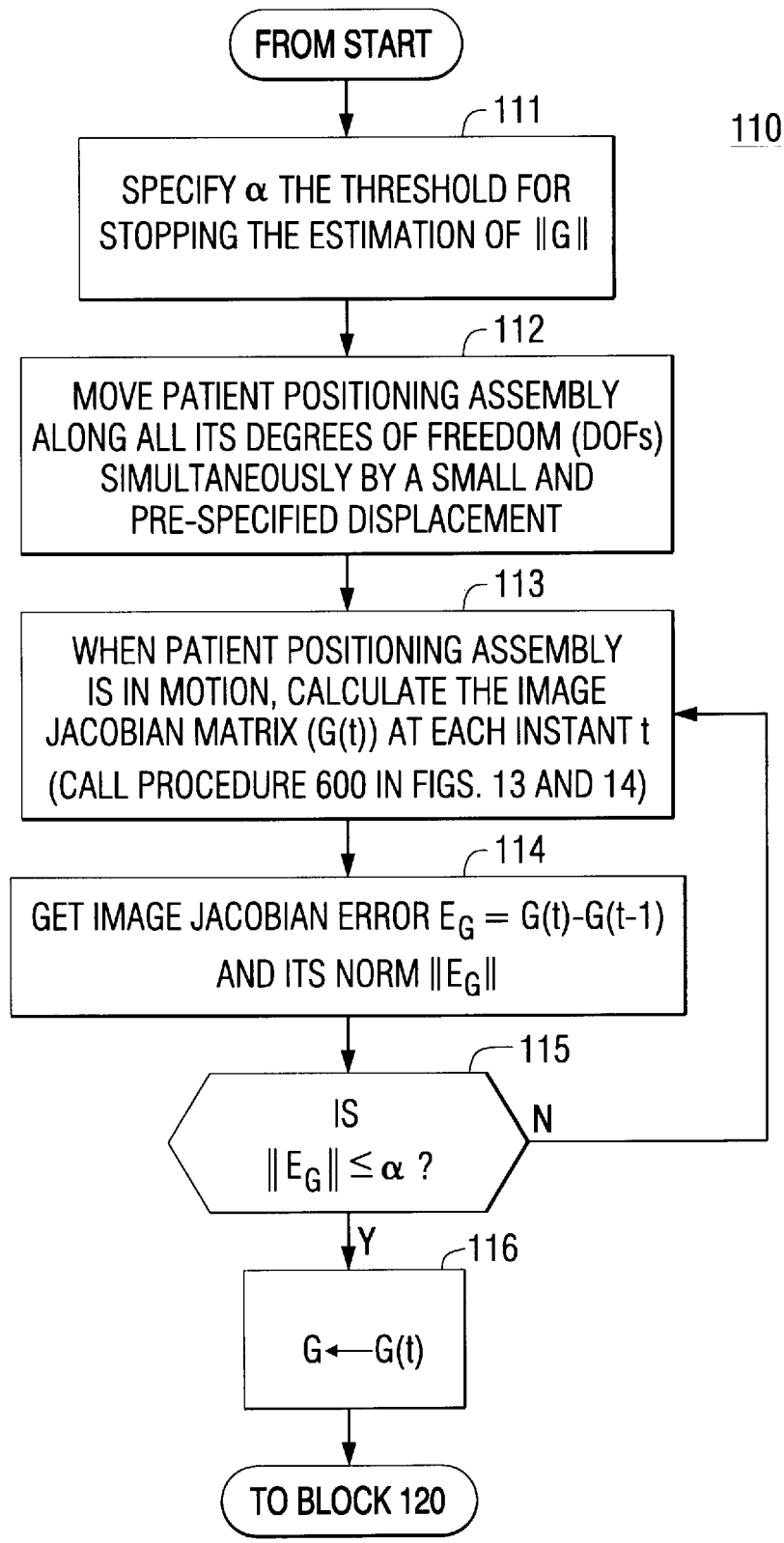

FIG. 7 illustrates the details of the block 300 of FIG. 1. The command velocity of the patient positioning assembly 23 in room space at each instant t is repetitively determined at 310. The details of this calculation will be explained in connection with FIG. 9. The command velocity is then applied to the motor control 65 of the patient positioning assembly 23 at 320. The new position error δ(t) is then determined at 330. The details of this determination are set forth in FIG. 10. If the vector norm of this new alignment error is small enough as determined at 340 in the manner described in detail in connection with FIG. 11, then the alignment is completed and the routine returns to block 400 in FIG. 1. Otherwise, the routine returns to block 310 and the calculation of the command velocity is repeated at the next time instant. This routine is repeated until the error is less than the threshold value.

The details of the initialization routine 110 of FIG. 5 are shown in FIG. 8. As mentioned previously, the Image Jacobian G is continuously refined in accordance with the invention. Rough values of the input parameters are used initially. The patient positioning assembly 23 is then moved simultaneously in all four degrees of freedom and the Image Jacobian G(t) is calculated repetitively, with each new calculation compared with the previous calculation to determine an error. As the calculation of G is refined the error is reduced until the error is less than a specified value. Thereafter the Image Jacobian will be updated whenever the current value of G differs from the previous value G(t−1) by a specified amount.

In the routine 110 shown in FIG. 8, α which is the desired threshold value for the error G is specified at 111. The patient positioning assembly 23 is then moved along all its degrees of freedom as indicated at 112 while the Image Jacobian G(t) is calculated at each instant t. The details of this routine 600 are explained in connection with FIGS. 13 and 14. The Image Jacobian error $E_G$ is then determined at 114 as the difference between the latest Image Jacobian and the most recent value. The norm of this error in the Jacobian is then compared to the threshold at 115. If the error is less than the threshold then the Image Jacobian is set to the latest value at 116. Otherwise, the Image Jacobian is further refined by looping back to 113.

Figure 9:
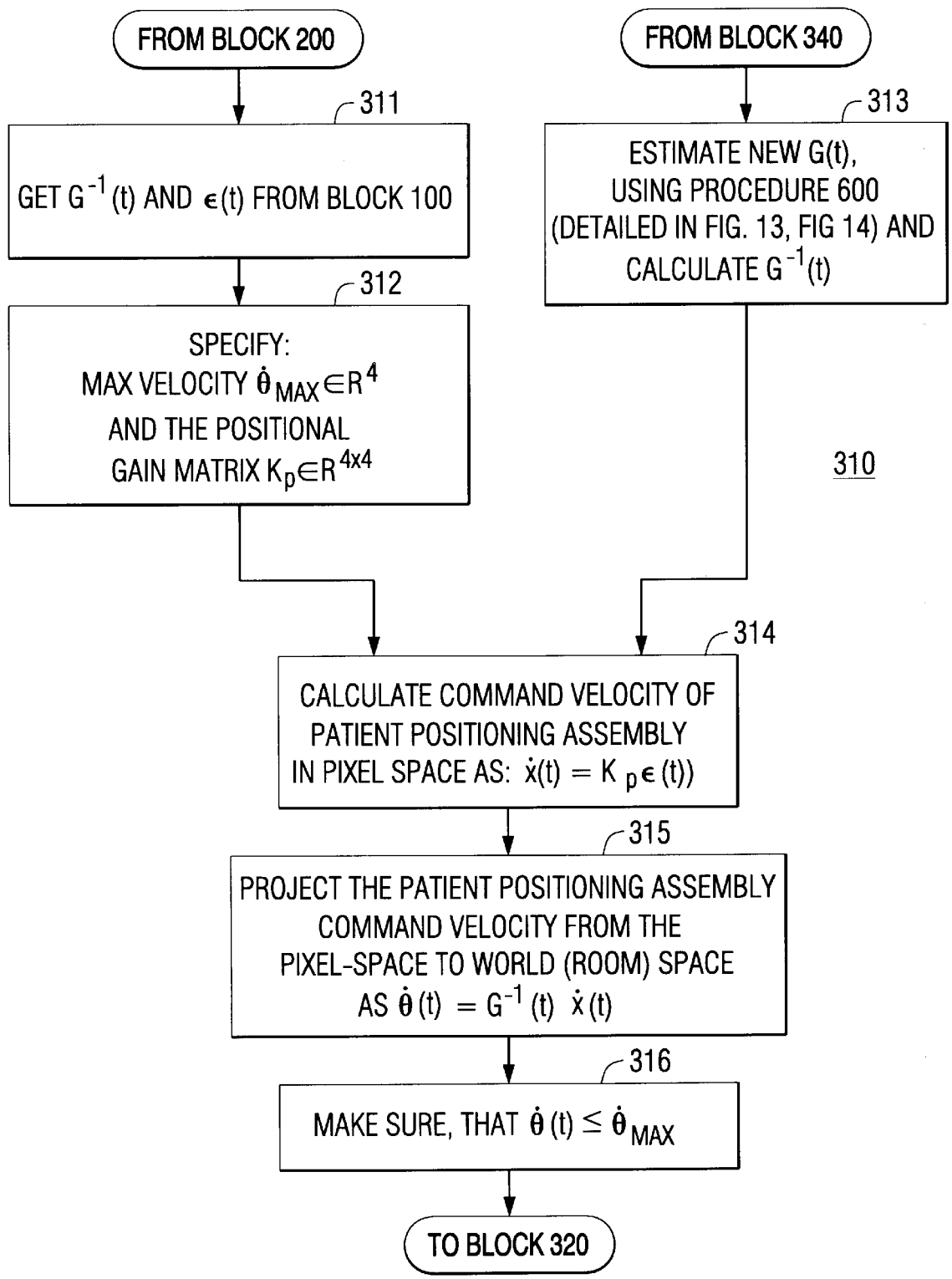

FIG. 9 provides the details of block 310 in FIG. 7 which generates the command velocity for the patient positioning assembly 23 in room space. On initial entry from block 200 from FIG. 4 the inverted Image Jacobian matrix $G^{-1}(t)$ and the position error in pixel space ε(t) are obtained at 311. The maximum velocity for the patient positioning assembly is then specified at 312 as a four-dimensional vector representing the four degrees of freedom of the patient positioning assembly. The 4×4 positional gain matrix $K_p$ is also specified. Where the error between the latest Image Jacobian and the previous Image Jacobian is not within limits (block 340) then the new Image Jacobian is estimated at block 313 using the procedure 600 detailed in FIGS. 13 and 14 and inverted. In either case, the command velocity for the patient positioning assembly in pixel space is calculated at 314 using the Equation 5 above. This is converted to a command velocity in room space at 315 using the inverse of the Image Jacobian. A check is made at 316 to assure that the command velocity does not exceed the specified maximum velocity.

Figure 10:
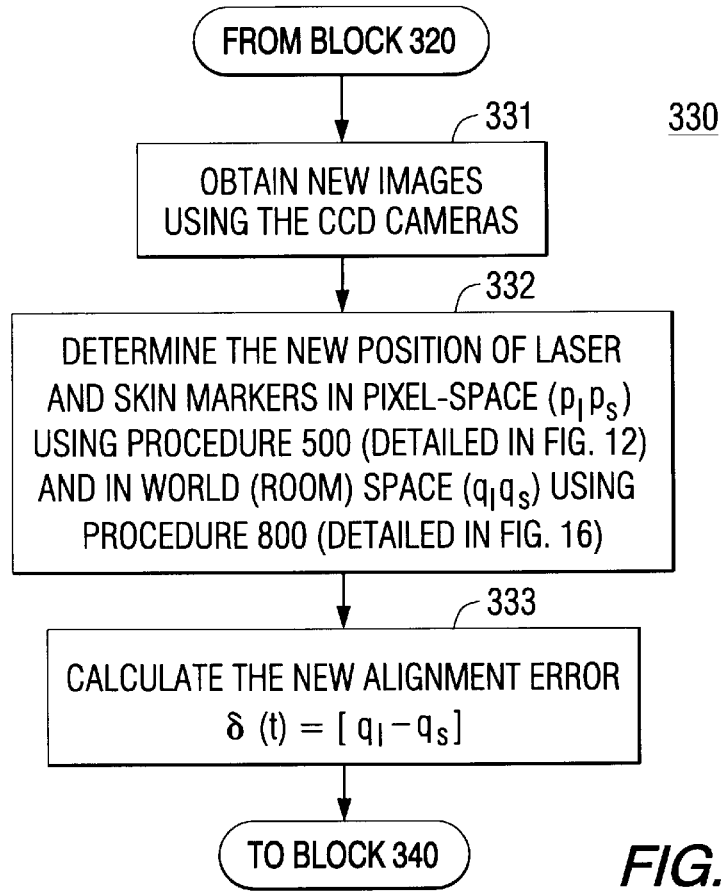

The details of the block 330 in FIG. 7 for determining the new alignment error is shown in FIG. 10. New camera images are obtained at 331 and used at 332 to determine the new position of the laser impingement points $p_l$ and fiducials $p_s$ in pixel space. The current positions of laser impingement points $q_l$ and fiducials $q_s$ in room space are also determined at 332 using machine encoder information. The alignment error in room space δ(t) is then calculated at 333.

Figure 11:
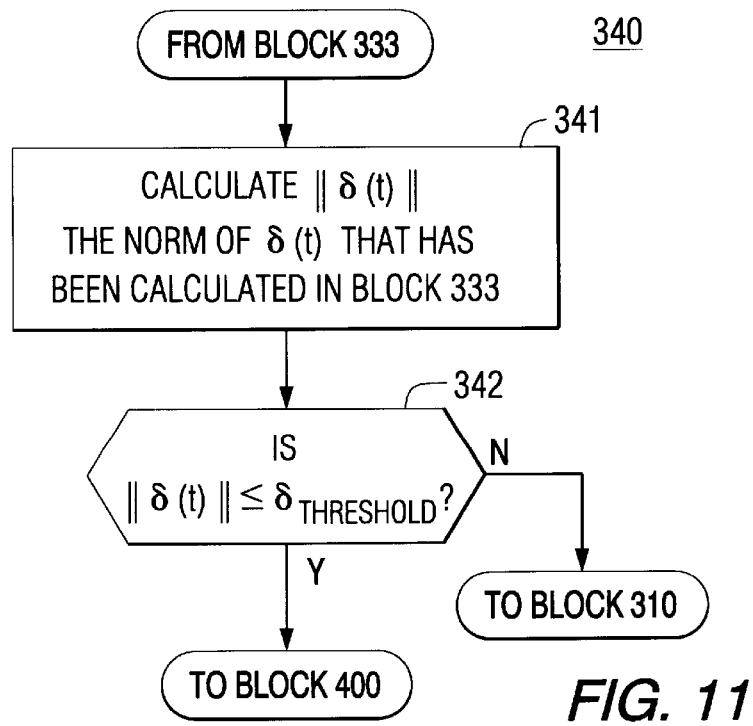

FIG. 11 shows the details of block 340 in FIG. 7. The norm of the alignment error in room space is calculated at 341 and compared to the threshold value for alignment error in 342. If the error is less than or equal to the threshold value, then the alignment is acceptable and the completion indication is output at block 400. If not, another iteration is initiated by a return to block 310 in FIG. 7.

Figure 12:
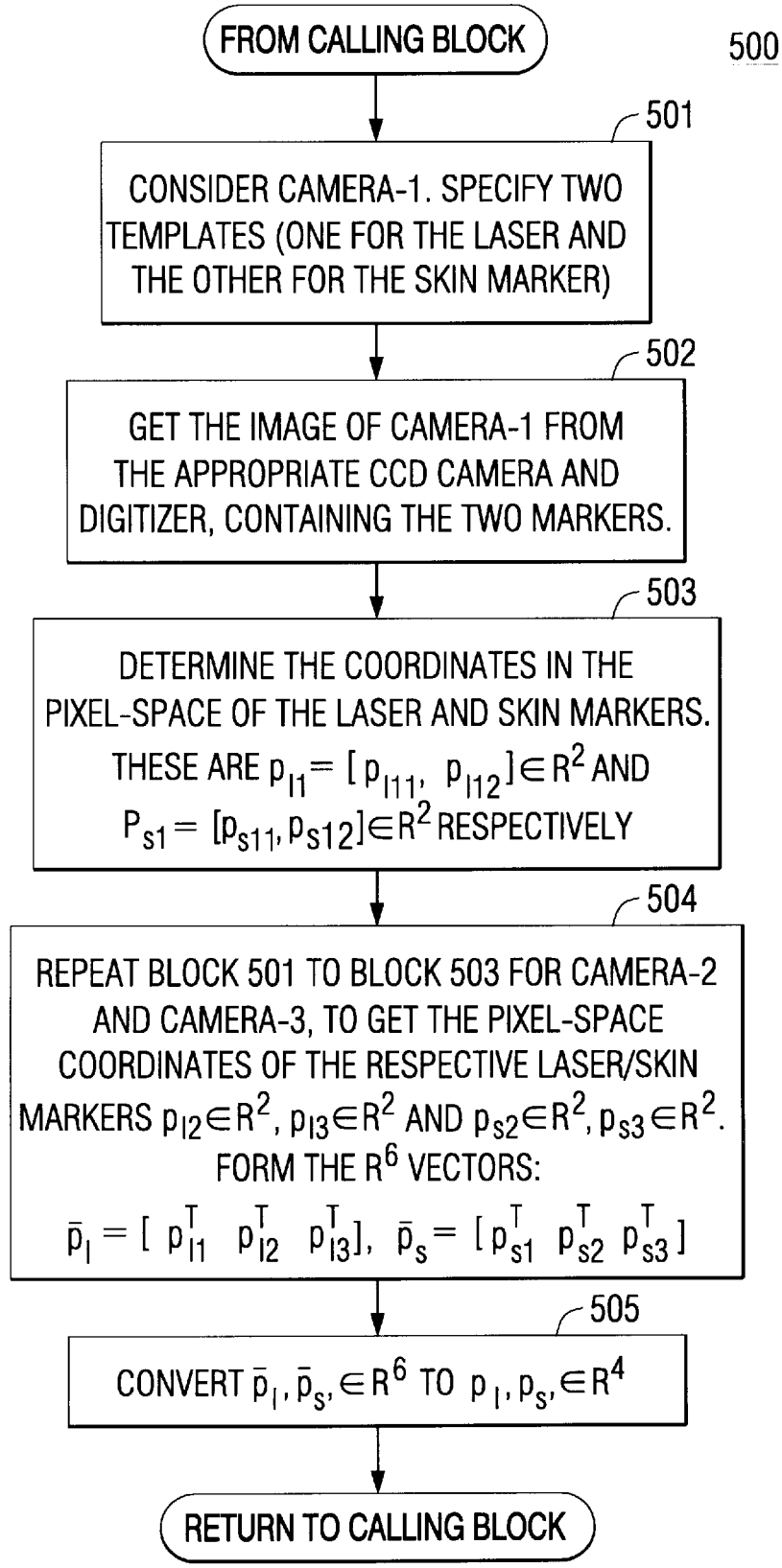

The procedure 500 for determining the position of the laser impingement points and fiducials in pixel space is shown in FIG. 12. For each camera, a template is specified for the laser impingement point and the fiducial at 501. The digitized image contained in the two markers is then obtained at 502 and used to determine the coordinates in pixel space of the laser impingement point and the fiducial in 503. Each of these points is defined by a two-dimensional vector. After these coordinates have been determined for each of the cameras, the six-dimensional vectors $\bar{p}_l$ and $\bar{p}_s$, respectively, are determined in 504. The six-dimensional vectors are then converted to four-dimensional vectors in block 505 in a manner discussed above.

Figure 13:
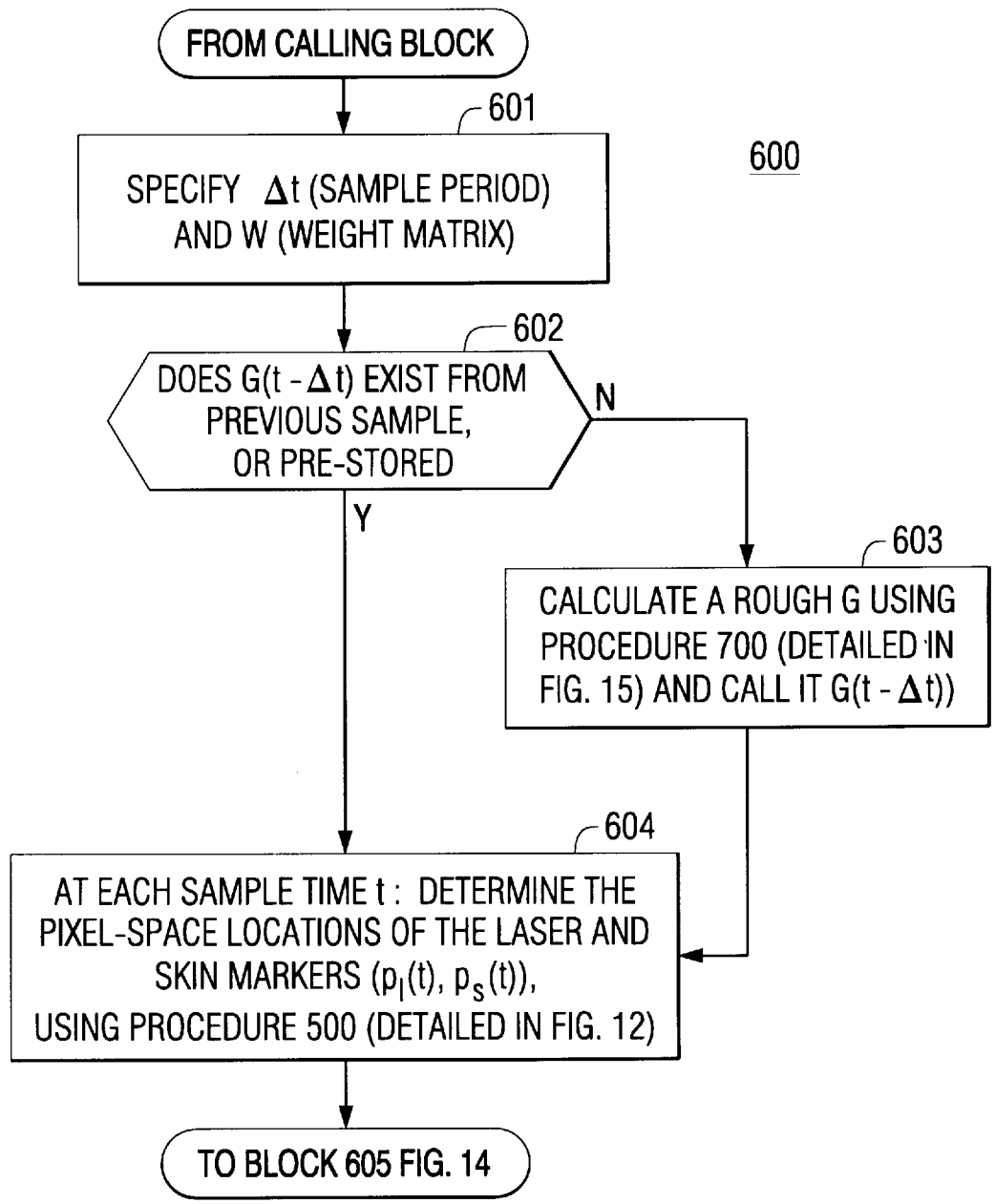
Figure 14:
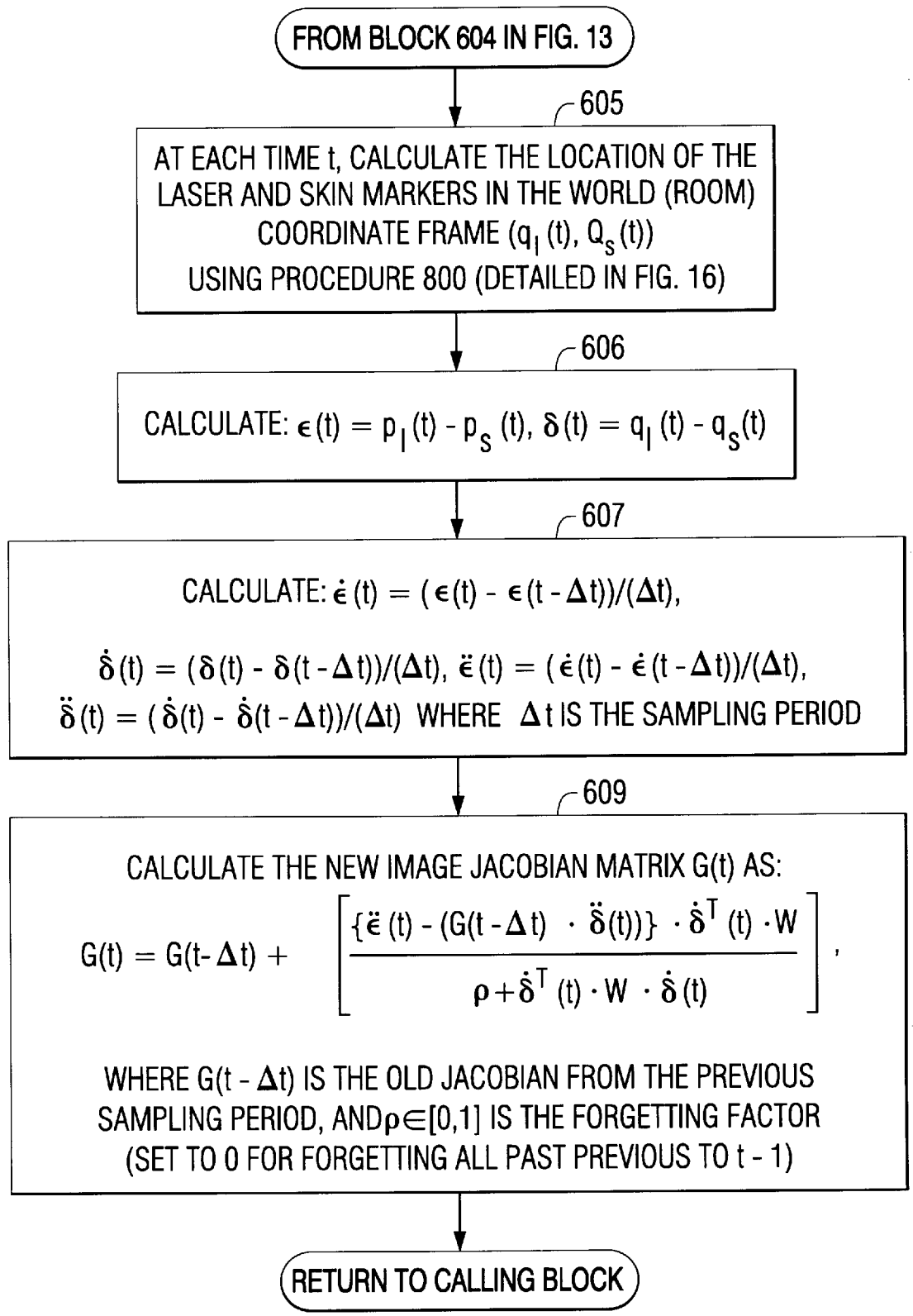
Figures 15, 16:
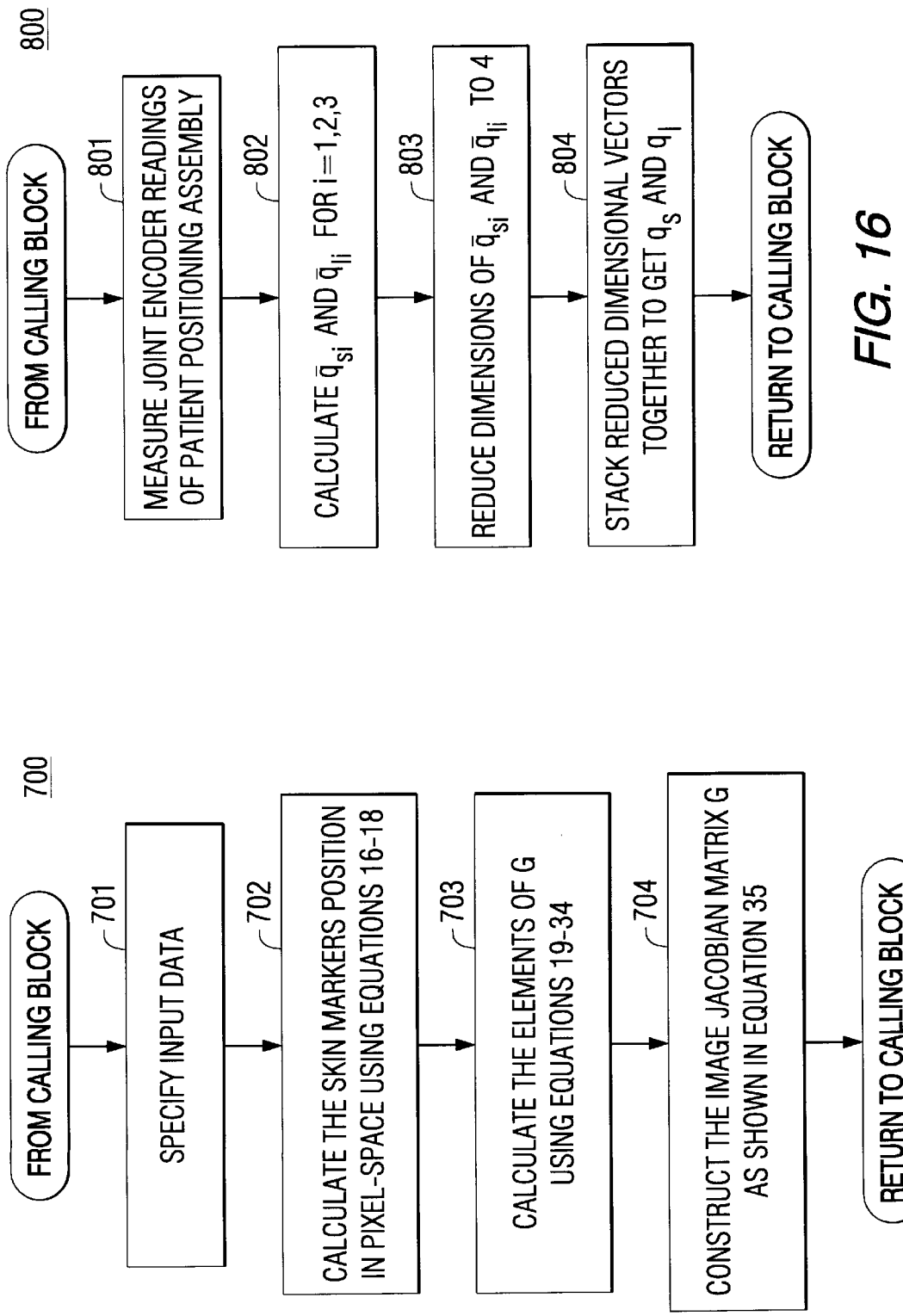

FIGS. 13 and 14 illustrate the procedure 600 used to update the Image Jacobian G. First, as shown at 601 the sample period Δt and W 4×4 weight matrix are specified. For the exemplary 30 Hz repetition rate, Δt is 33 msec. If as determined at 602 a previous sample or pre-stored value of the Image Jacobian, G(t−Δt) does not exist then a rough matrix is calculated at 603 using the procedure 700, the details of which are shown in FIG. 15. Whichever way G(t−Δt) is established, the locations of the laser impingement points and fiducials in pixel space at sample times t occurring at the intervals Δt are calculated at 604 using the procedure 500 just described. The locations of the laser impingement points and the fiducials in room space are then determined at 605 using the position of the patient positioning assembly 23 in its 4 degrees of freedom from the position encoders and the procedure 800 illustrated in FIG. 16. The position error ε(t) in pixel space and the error δ(t) in room space are then calculated in block 606 from the respective sets of coordinates. Current velocity errors in pixel space and in room space are then determined at block 607 from the differences between the current positions and the last positions divided by the sample time Δt. Acceleration errors ε(t) and δ(t) are also calculated in block 607. The new Image Jacobian matrix G(t) is calculated in block 609 as being equal to the last image Jacobian, G(t−Δt) plus an incremental matrix. This incremental matrix is determined as an acceleration error in pixel space $\epsilon(t)$ minus the prior Image Jacobian multiplied by a current acceleration error in room space $\delta(t)$. The result which is a column vector is converted to a matrix by the transpose $\delta^T(t)$ multiplied by the weight matrix W. This is all then divided by a quantity which includes the factor $\rho$ plus the velocity error in room space $\delta(t)$ multiplied by the weighing matrix W and the transform $\delta^T(t)$. The $\rho$ is a scalar which is known as a forgetting factor. When $\rho$ is set to 0 all previous calculations of G except the last are forgotten. When $\rho$ is set to 1, all past calculations are retained.

The procedure 700 for constructing the initial Image Jacobian is shown in FIG. 15. The input data indicated above as items i–iv are specified at 701. The positions of the fiducials in pixel space are then determined at 702 using the equations 16–18 above. The elements of the Image Jacobian matrix are then calculated using the equations 19–34 at 703. Equation 35 is then used at 704 to construct the Image Jacobian matrix G.

FIG. 16 illustrates the procedure 800 for determining the positions for the fiducials or skin markers and the laser markers or impingement points in room space. As indicated at 801 the readings of the joint encoders of the patient positioning assembly are taken. These readings are used to calculate the coordinates of the fiducials and laser impingement points at 802. The routine shown is generalized. In the exemplary embodiment of the invention, as discussed above, the coordinates of the laser impingement points are always all zeros, and therefore, need not be calculated. The six-dimensional vectors calculated in 802 are reduced to four-dimensional vectors in 803 in accordance with the procedure described above. These reduced dimensional vectors are then stacked at 804 to generate the position of the fiducials $q_s$ and in the general case laser markers $q_l$, in room space.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. Apparatus for automatically, accurately positioning a patient reclining on a moveable patient positioning assembly to a fixed base position relative to a fixed reference of a treatment/diagnostic device, said apparatus comprising:
   a plurality of spaced apart fiducials arranged on said patient;
   laser beam generator means for generating a plurality of laser beams projected in different directions relative to said fixed reference to impinge on the patient at impingement points which coincide with said fiducials when said patient is at said fixed base position;
   camera means for generating images of said fiducials and said impingement points; and
   means generating control signals from said images for driving said moveable patient positioning assembly to bring said fiducials into coincidence with said impingement points, thereby positioning said patient at said fixed base position.

2. The apparatus of claim 1 wherein said plurality of fiducials comprise three fiducials arranged on said patient in a common first plane and wherein said laser beam generator means comprises means generating three laser beams projected in different directions in a common reference plane.

3. The apparatus of claim 2 wherein said treatment/diagnosis device has a treatment plane and wherein said common reference plane is coincident with said treatment plane.

4. The apparatus of claim 1 wherein said means generating control signals from said images control signals comprises means generating signals in pixel space of said camera means including position signals representative of positions of said fiducials and said laser impingement points in pixel space and means generating control signals in room space from said signals in pixel space including means applying conversion means converting signals in pixel space to signals in room space.

5. The apparatus of claim 4 wherein said means applying conversion means comprises means continuously refining said conversion means.

6. The apparatus of claim 5 wherein said means continuously refining said conversion means comprises means establishing a last conversion means, means setting said patient positioning assembly in motion, means repetitively determining present position error of said fiducials relative to said laser impingement points in pixel space at specified sample times, means repetitively determining a present position error between said fiducials and said laser impingement points in room space at said sample times, and means updating said conversion means from said present position error in pixel space and said present position error in room space.

7. The apparatus of claim 5 wherein said means generating control signals from said images includes means repetitively generating a velocity error signal in pixel space from said position signals in pixel space, and wherein said conversion means comprises velocity conversion means converting said velocity error signal in pixel space to a velocity error signal in room space for controlling driving said patient positioning assembly to bring said fiducials into coincidence with said impingement points.

8. The apparatus of claim 5 adapted for use with a treatment/diagnostic device having a patient positioning assembly with multiple degrees of freedom and position encoder means generating outputs indicating position of said patient positioning assembly in said multiple degrees of freedom in room space, wherein said means continuously refining said conversion means comprises means establishing a rough initial value for said conversion means and means for repetitively determining a present position error of said fiducials relative to said laser impingement points in pixel space from said images of said fiducials and said impingement points, means repetitively determining a present position error between said fiducials and said laser impingement points in room space from said outputs of said position encoders, and means updating said conversion means from said present position error in pixel space and said present position error in room space.

9. The apparatus of claim 4 wherein said means generating signals in pixel space comprises means generating a position error signal representing error between positions of said fiducials and said laser impingement points in pixel space, means generating a velocity error signal in pixel space from said position error signal in pixel space, and wherein said conversion means comprises velocity conversion means converting said velocity error signal in pixel space to a velocity error signal in room space.

10. The apparatus of claim 5 wherein said means generating signals in pixels space comprises means generating said position signals repetitively at sampling intervals, said means generating control signals in room space comprises means generating a velocity error signal in pixel space from said position signals, repetitively at said sampling intervals, said means applying said conversion means comprises means applying an inverse of an Image Jacobian G to said velocity error signal in pixel space to generate a velocity error signal in room space for driving said movable patient positioning assembly, and said means continuously refining said conversion means comprises means repetitively at said sampling intervals updating said Image Jacobian according to the relationship:

$$G(t) = G(t - \Delta t) + \left[ \frac{\ddot{\epsilon}(t) - (G(t - \Delta t) \cdot \ddot{\delta}(t)) \cdot \dot{\delta}^T(t) \cdot W}{\rho + \delta^T(t) \cdot W \cdot \dot{\delta}(t)} \right]$$

wherein G(t) is an updated Image Jacobian at a present sampling interval, G(t−Δt) is the Image Jacobian from a most recent sampling period, $\epsilon(t)$ is a present acceleration error in pixel space determined from said position error signals in pixel space, $\dot{\delta}(t)$ is a present velocity error in room space, $\ddot{\delta}(t)$ is a present acceleration error in room space, $\delta^T$ is a transform, W is a weighing matrix and $\rho$ is a forgetting factor.

11. The apparatus of claim 4 wherein said means applying conversion means comprises means requiring no detailed calibration of said cameras.

12. The apparatus of claim 11 wherein said means requiring no detailed calibration of said cameras comprises means establishing a rough initial value for said conversion means, and means for continuously refining said conversion means.

* * * * *

UNITED STATES PATENT AND TRADEMARK OFFICE
CERTIFICATE OF CORRECTION

PATENT NO.   : 5,823,192
DATED        : October 20, 1998
INVENTOR(S)  : Andre M. Kalend et al.

It is certified that error appears in the above-identified patent and that said Letters Patent is hereby corrected as shown below:

Column 4,
Line 47, "$^{47}{}_1$" should read -- $47_1$ --.

Column 7,
Line 7, insert -- Eq. -- prior to "9".
Line 11, insert -- Eq. -- prior to "10".
Line 13, insert -- Eq. -- prior to "11".
Line 15, insert -- Eq. -- prior to "12".
Line 18, remove "and $q_{,3z}$".
Line 22, insert -- Eq. -- prior to "13".
Line 33, insert -- Eq. -- prior to "14".
Line 35, insert -- Eq. -- prior to "15".

Column 10,
Line 64, "$\epsilon(t)$" should read -- $\ddot{\epsilon}(t)$ --
Line 64, "$\delta(t)$" should read -- $\ddot{\delta}(t)$ --

Column 11,
Line 1, "$\epsilon(t)$" should read -- $\ddot{\epsilon}(t)$ --
Line 3, "$\delta(t)$" should read -- $\ddot{\delta}(t)$ --

Column 12,
Line 6, delete "control signals" before "comprises".
Line 64, "pixels" should read -- pixel --.

UNITED STATES PATENT AND TRADEMARK OFFICE
CERTIFICATE OF CORRECTION

PATENT NO.   : 5,823,192
DATED        : October 20, 1998
INVENTOR(S)  : Andre M. Kalend et al.

It is certified that error appears in the above-identified patent and that said Letters Patent is hereby corrected as shown below:

Column 13,
Line 16, "$\epsilon(t)$" should read -- $\ddot{\epsilon}(t)$ --

Column 14,
Line 3, "$\delta(t)$" should read -- $\ddot{\delta}(t)$ --

Signed and Sealed this

Eighth Day of October, 2002

Attest:

Attesting Officer

JAMES E. ROGAN
Director of the United States Patent and Trademark Office